(12) United States Patent
Lin et al.

(10) Patent No.: US 8,957,381 B2
(45) Date of Patent: Feb. 17, 2015

(54) SHOCKPROOF GAS SENSOR

(71) Applicant: Radiant Innovation Inc., Hsinchu (TW)

(72) Inventors: Tseng-Lung Lin, Hsinchu County (TW); Chin-Hui Ku, Kaohsiung (TW)

(73) Assignee: Radiant Innovation Inc., Hsinchu (TW)

( * ) Notice: Subject to any disclaimer, the term of this patent is extended or adjusted under 35 U.S.C. 154(b) by 70 days.

(21) Appl. No.: 13/917,888

(22) Filed: Jun. 14, 2013

(65) Prior Publication Data
US 2014/0367574 A1    Dec. 18, 2014

(51) Int. Cl.
*G01N 21/61*    (2006.01)
(52) U.S. Cl.
CPC ........................... *G01N 21/61* (2013.01)
USPC .......................................................... 250/343
(58) Field of Classification Search
CPC ............................ G01N 21/3504; G01N 21/61
USPC .......................................................... 250/343
See application file for complete search history.

(56) References Cited

U.S. PATENT DOCUMENTS

| | | | | |
|---|---|---|---|---|
| 5,464,982 A | * | 11/1995 | Drucker et al. | 250/343 |
| 5,613,294 A | * | 3/1997 | Ferran | 29/825 |
| 7,285,782 B2 | * | 10/2007 | Schubert | 250/339.13 |
| 2008/0173817 A1 | * | 7/2008 | Goldstein et al. | 250/338.1 |
| 2012/0170023 A1 | * | 7/2012 | Szobota et al. | 356/51 |

* cited by examiner

*Primary Examiner* — Marcus Taningco
(74) *Attorney, Agent, or Firm* — Rosenberg, Klein & Lee

(57) ABSTRACT

A shockproof gas sensor includes a gas detector, an infrared source, an infrared detector a circuit board and at least one shockproof unit. The gas detector defines a chamber, a first end portion and a second end portion opposite the first end portion. The infrared source is disposed in the chamber proximate to the first end portion while the infrared detector is disposed in the chamber and proximate to the second end portion. The circuit board is respectively electrically connected to the infrared source and the infrared detector. The shockproof unit is coupled to the gas detector and the circuit board, and the gas detector is secured on the circuit board by the shockproof unit.

10 Claims, 10 Drawing Sheets

SHOCKPROOF GAS SENSOR

BACKGROUND

1. Field of the Invention

The instant disclosure relates to a gas sensor; in particular, to a shockproof gas sensor.

2. Description of Related Art

The conventional carbon dioxide sensor or analyzer uses non-dispersive infrared (NDIR) absorption to detect gas concentration. The gas absorbs infrared within a specific range of light spectrum and the amount of absorption is directly proportional to the gas concentration. For example, carbon monoxide shows absorption peak at 4.7 μm and carbon dioxide at 4.3 μm. The different absorption peak is used to detect a specific gas concentration. Namely, different states of gas molecules have their corresponding vibrational energy level. When a gas molecule is excited by the radiation having the corresponding vibrational energy, the gas molecule absorbs the energy and the amount of absorption of the radiation is directly proportional to the molecule concentration.

However, the conventional gas sensor emphasizes the detection speed instead of the shockproof property. When the radiation emitter or the sensor encounters shocks or crash, the filament might be distorted, further compromising the measurement precision. Therefore, providing a shockproof gas sensor is a current issue in the industry.

SUMMARY OF THE INVENTION

The instant disclosure provides a shockproof gas sensor. According to one embodiment of the instant disclosure, the shockproof gas sensor includes a gas detector, an infrared source, an infrared detector, a circuit board and at least one shockproof unit. The gas detector defines a chamber, a first end portion and a second end portion opposite the first end portion. The infrared source is disposed in the chamber proximate to the first end portion while the infrared detector is disposed in the chamber and proximate to the second end portion. The circuit board is electrically connected to the infrared source and the infrared detector respectively. The shockproof unit is coupled to the gas detector and the circuit board, and the gas detector is secured on the circuit board by the shockproof unit.

Preferably the shockproof unit includes a plurality of knobs and a buffer portion that sleeves the outer face of the chamber, and the circuit board is formed with a plurality of alignment holes for receiving the plurality of knobs in place.

Preferably the shockproof unit sleeves the outer face of the chamber and an adhesive layer is formed between the shockproof unit and the circuit board for tightly connecting the shockproof unit and the circuit board, and the adhesive layer is formed by adhesive dripping on the circuit board.

Preferably two shockproof units sleeve the gas detector, and one of the shockproof units is coupled to the outer face of the chamber proximate to the first end portion while the other one of the shockproof units is coupled to the outer face of the chamber proximate to the second end portion.

Preferably a plurality of shockproof units sleeves the gas detector and each of the shockproof units is spaced by a predetermined distance between the first and second end portions.

Preferably the two shockproof units further have a connection portion connecting therebetween, and the connection portion is disposed between the chamber and the circuit board and connected to the chamber and the circuit board.

According to another embodiment of the instant disclosure, the shockproof gas sensor includes a gas detector, an infrared source, an infrared detector, a reflector, a circuit board and at least one shockproof unit. The gas detector defines an upper chamber, a lower chamber opposite to the upper chamber, a first end portion and a second end portion opposite the first end portion. The infrared source is disposed in the chamber proximate to the first end portion. The infrared detector is disposed in the chamber and proximate to the second end portion. The circuit board is electrically connected to the infrared source and the infrared detector respectively. The shockproof unit is coupled to the gas detector and the circuit board. The gas detector is secured on the circuit board by the shockproof unit. The reflector is coupled to the second end portion and connecting the upper and lower chambers.

Preferably two shockproof units sleeve the gas detector, and one of the shockproof units is coupled to the outer face of the upper and lower chambers proximate to the first end portion while the other one of the shockproof units is coupled to the outer face of the upper and lower chambers proximate to the second end portion.

Preferably a plurality of shockproof units sleeves the gas detector and is spaced by a predetermined distance between the first and second end portions.

Preferably the two shockproof units further have a connection portion connecting therebetween, and the connection portion is disposed between the chamber and the circuit board and connected to the chamber and the circuit board.

In summary, the shockproof gas sensor of the instant disclosure prevents the infrared detector from shifting or the infrared source from distortion upon shock or crash. The infrared distribution and the measurement precision are therefore maintained. This stability is supported by the shockproof unit connecting to the gas detector and the circuit board.

In order to further understand the instant disclosure, the following embodiments are provided along with illustrations to facilitate the appreciation of the instant disclosure; however, the appended drawings are merely provided for reference and illustration, without any intention to be used for limiting the scope of the instant disclosure.

DETAILED DESCRIPTION OF THE PREFERRED EMBODIMENTS

The aforementioned illustrations and following detailed descriptions are exemplary for the purpose of further explaining the scope of the instant disclosure. Other objectives and advantages related to the instant disclosure will be illustrated in the subsequent descriptions and appended drawings.

First Embodiment

Figure 1:
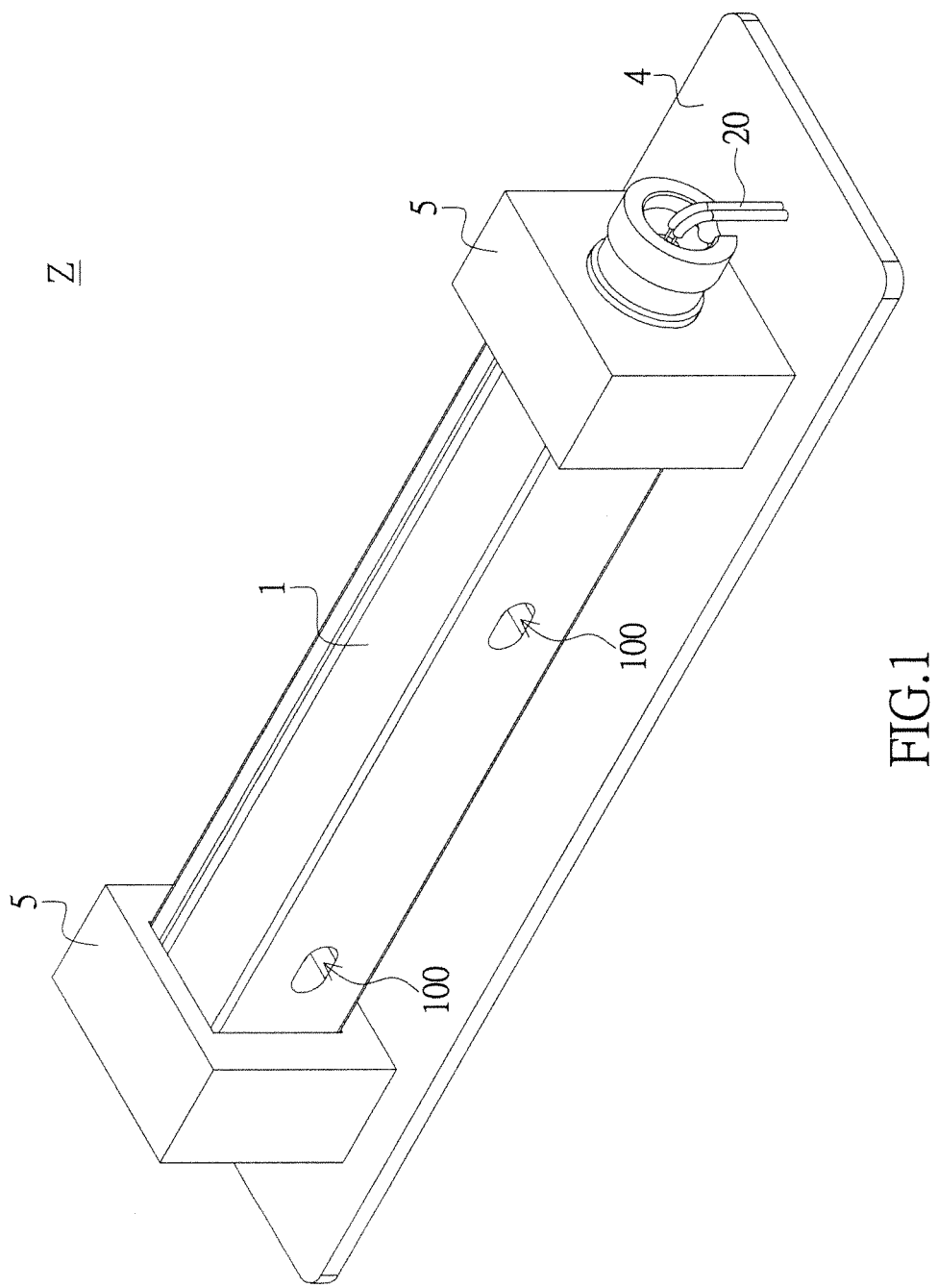
FIG. 1 is a perspective view of a gas sensor in accordance with a first embodiment of the instant disclosure.
Figure 2A:
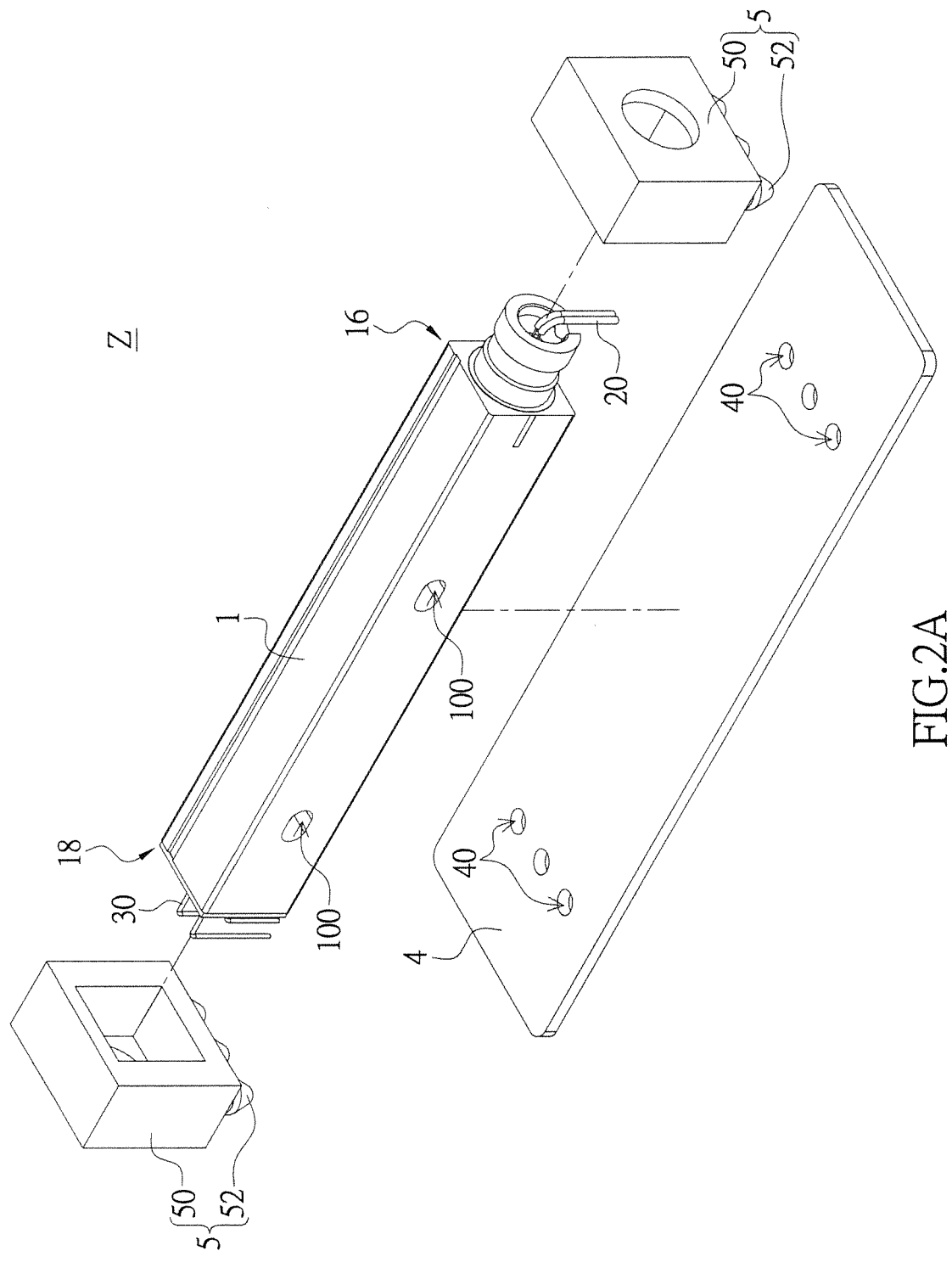
FIG. 2A is an exploded view of a gas sensor in accordance with a first embodiment of the instant disclosure.
Figure 2B:
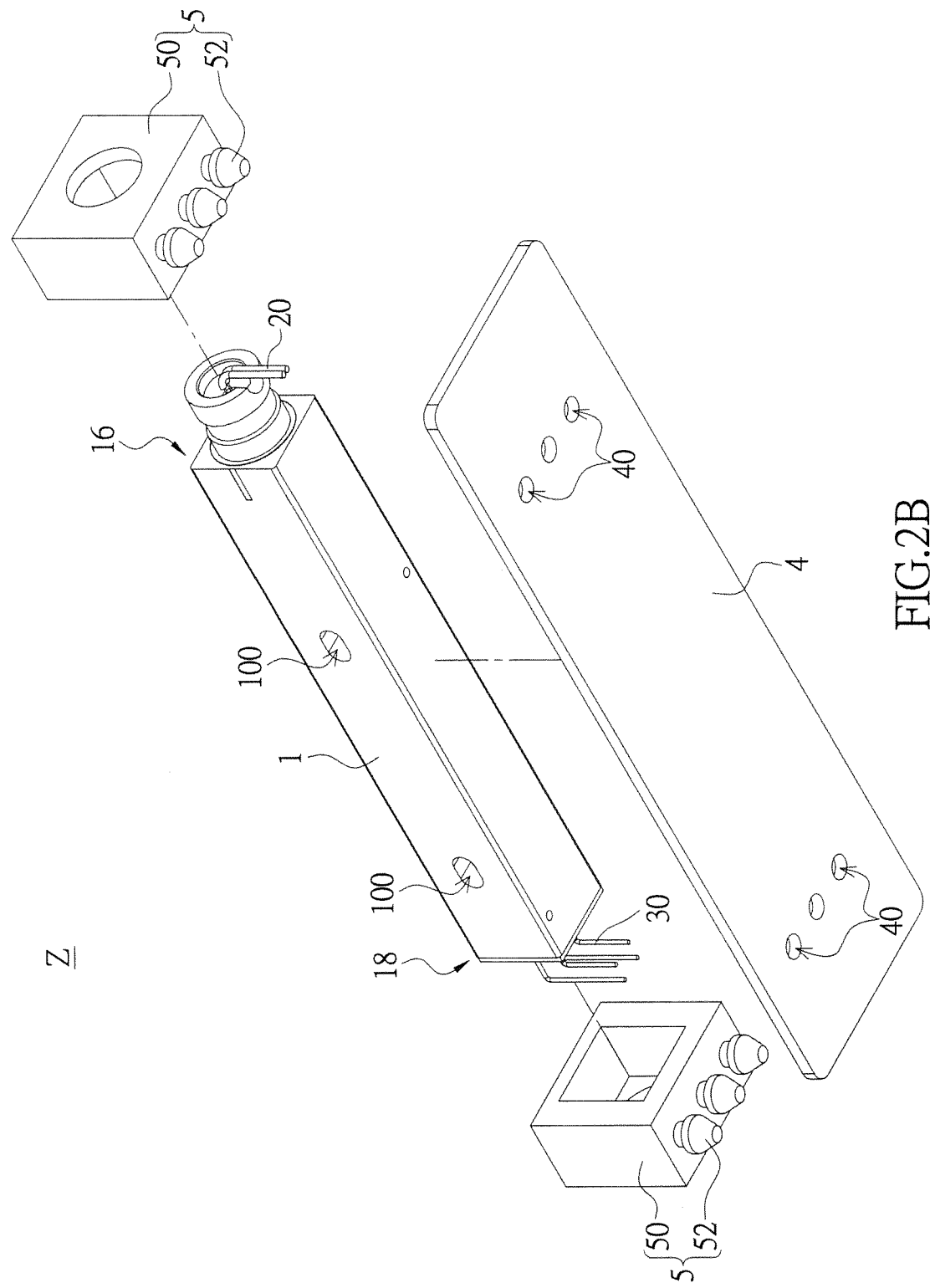
FIG. 2B is another exploded view of a gas sensor in accordance with a first embodiment of the instant disclosure.
Figure 3:
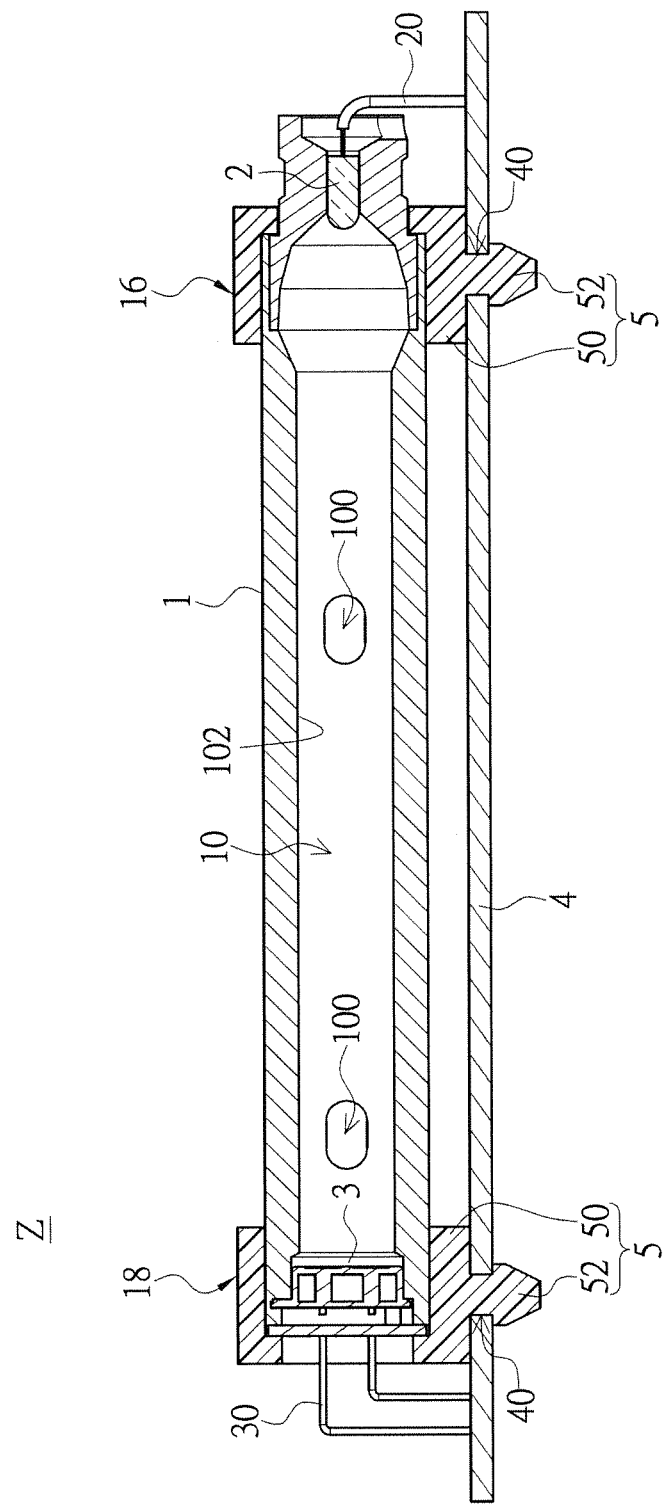
FIG. 3 is a cross-sectional view of a gas sensor in accordance with a first embodiment of the instant disclosure.

Please refer to FIGS. 1 to 3. FIG. 1 is a perspective view of a gas sensor Z. FIG. 2A is an exploded view of the gas sensor Z. FIG. 2B is another exploded view of the gas sensor Z. FIG. 3 is a cross-sectional view of the gas sensor Z. According to a first embodiment of the instant disclosure, the gas sensor Z includes a gas detector 1, an infrared source 2, an infrared detector 3, a circuit board 4, and at least one shockproof unit 5. Referring to FIGS. 1 to 3, the gas detector 1 defines a chamber 10 and has a first end portion 16 and a second end portion 18 opposite the first end portion 16. The infrared source 2 and the infrared detector 3 are respectively disposed on the end portions of the chamber 10. The circuit board 4 is electrically connected to a display unit, a control unit and a processing unit (not shown). Conventional connection means between the circuit board 4 and the electronic components are well known to those skilled in the art and they may be employed to the instant disclosure.

Referring to FIGS. 1 to 3, the chamber 10 forms a single gas channel, and at least one air window 100 is formed on the chamber 10 for admitting gas therein. The air window 100 may be equipped with filters or nonwoven fabrics (not shown). The filters or nonwoven fabrics can prevent undesired particles from entering the chamber 10 and affecting the measurement precision. The gas under detection is allowed entry to the chamber 10 and the gas may be carbon dioxide, carbon monoxide, or the combination of the two. The inner face of the chamber 10 is formed with a reflective layer 102. The reflective layer 102 may be formed on the inner face of the chamber 10 by electroplating. The reflective layer 102 may be made of gold-containing metal, nickel-containing metal, gold, nickel or an alloy thereof.

Furthermore, referring to FIGS. 1 to 3, the infrared source 2 is disposed in the chamber 10 proximate to the first end portion 16. The infrared source 2 emits infrared light beams to the gas channel and the light propagates further as being repeatedly reflected by the reflective layer 102. Meanwhile, the gas absorbs light ranging in a specific wavelength. (For example, carbon monoxide shows absorption peak at 4.7 µm and carbon dioxide at 4.3 µm.) In general, the infrared is used because it is relatively cost effective and produces less heat.

Referring to FIGS. 1 to 3, the infrared detector 3 is disposed in the chamber 10 proximate to the second end portion 18. The infrared detector 3 receives the infrared reflected by the reflective layer 102 but not absorbed by the gas. The gas concentration can be obtained according to the infrared intensity detected by the infrared detector 3.

Referring to FIGS. 1 to 3, the circuit board 4 is a printed circuit board (PCB). The infrared source 2 and the infrared detector 3 are respectively electrically connected to the circuit board 4. Specifically, the infrared source 2 has a connection wire 20 and the infrared detector 3 has a connection wire 30. The connection wires 20, 30 are securely welded to the circuit board 4 to prevent the connection wires 20, 30 from disconnection caused by external forces.

Referring to FIGS. 1 to 3, the shockproof unit 5 retains the gas detector 1, infrared source 2, infrared detector 3 and circuit board 4 thereon. The shockproof unit 5 is connected to the gas detector 1 and the circuit board 4. Specifically, the gas detector 1 is coupled to the circuit board 4 via the shockproof unit 5.

In the instant embodiment, the shockproof unit 5 includes a buffer portion 50, which caps the outer face of the chamber 10, and a plurality of knobs 52. The shockproof unit 5 may be made of soft rubber, elastic materials or the combination thereof. The circuit board 4 is formed with a plurality of alignment holes 40 for receiving the knobs 52. Through the mating between the knobs 52 and the alignment holes 40, the circuit board 4 and the shockproof unit 5 are mated to each other.

It is worth mentioning that in the instant embodiment the gas detector 1 has a pair of shockproof unit 5. One of the shockproof units 5 is coupled to the outer face of the chamber 10 proximate to the first end portion 16 while the other shockproof unit 5 is couple to the outer face of the chamber 10 proximate to the second end portion 18. The knob 52 resembles a cone and the dimension is slightly larger than that of the alignment hole 40 to provide a secure engagement. Each shockproof unit 5 has at least one knob 52. In another embodiment, the shockproof unit 5 may be in other configuration, for example, rectangular block, cylinder or the like. The shockproof unit 5 is also connected to the circuit board 4. The shockproof unit 5 in general absorbs shock from the gas detector 1 regardless the shape thereof. The shape of the knob 52 is not limited to the instant embodiment.

Second Embodiment

Figure 4:
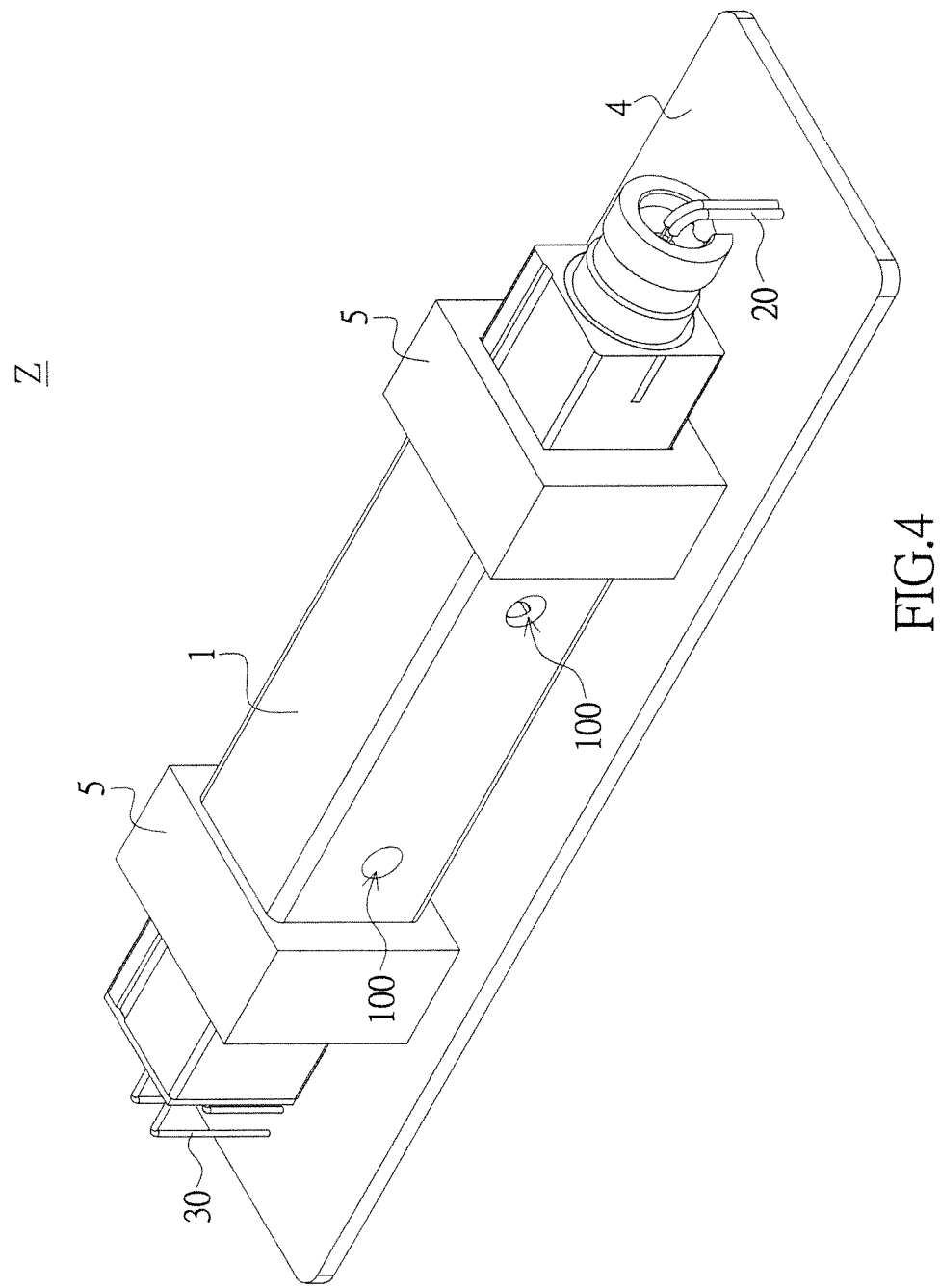
FIG. 4 is a perspective view of a gas sensor in accordance with a second embodiment of the instant disclosure.
Figure 5:
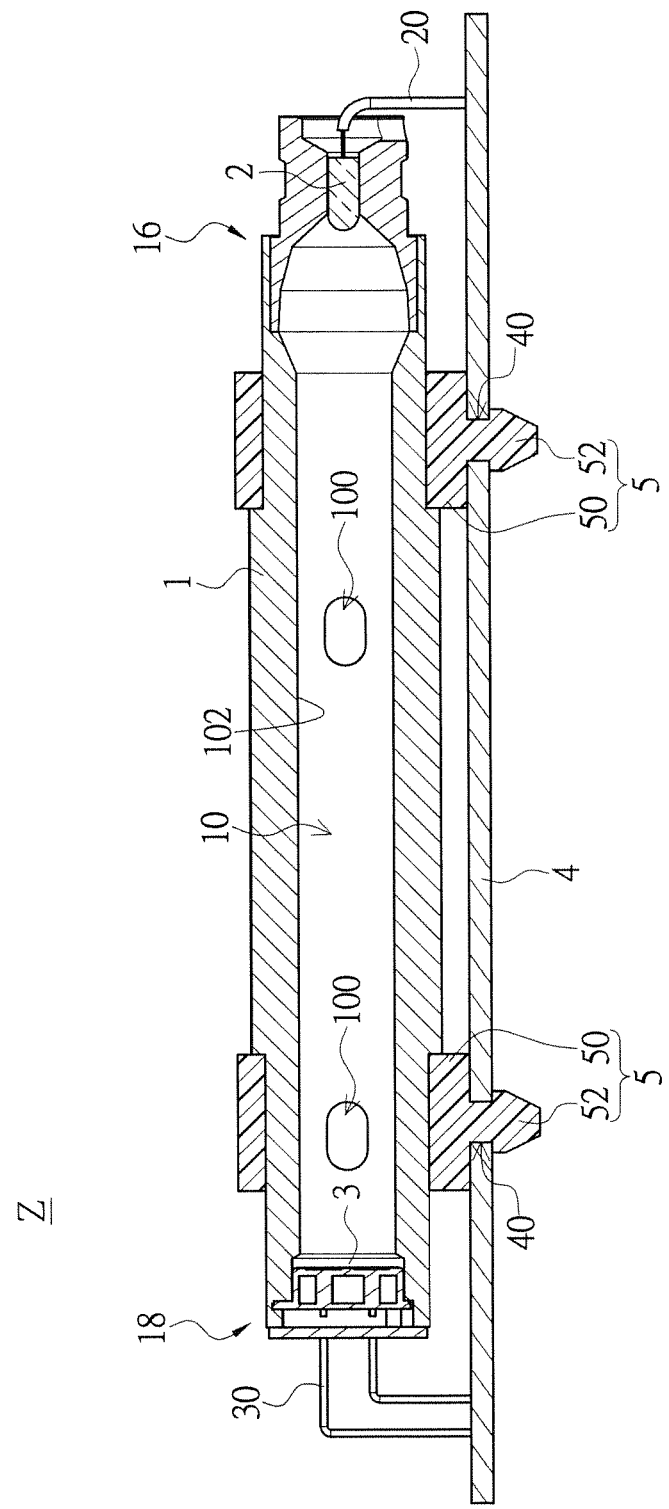
FIG. 5 is a cross-sectional view of a gas sensor in accordance with a second embodiment of the instant disclosure.

Please refer to FIGS. 4 to 5. FIG. 4 is a perspective view of the gas sensor Z. FIG. 5 is a cross-sectional view of the gas sensor Z. Comparing FIGS. 1 to 4 and 3 to 5, the gas sensor Z of the second embodiment includes a gas detector 1, an infrared source 2, an infrared detector 3, a circuit board 4, and at least one shockproof unit 5. The main difference between the first and the second embodiment arises from the shockproof unit 5 arrangement. In the second embodiment, the gas detector 1 has the plurality of shockproof units 5. Each shockproof unit 5 is disposed between the first and second end portions 16, 18 and separated from each other by a predetermined distance.

The even arrangement of the shockproof units 5 around the outer face of the chamber 10 provides desirable shock absorption result.

Third Embodiment

Figure 6:
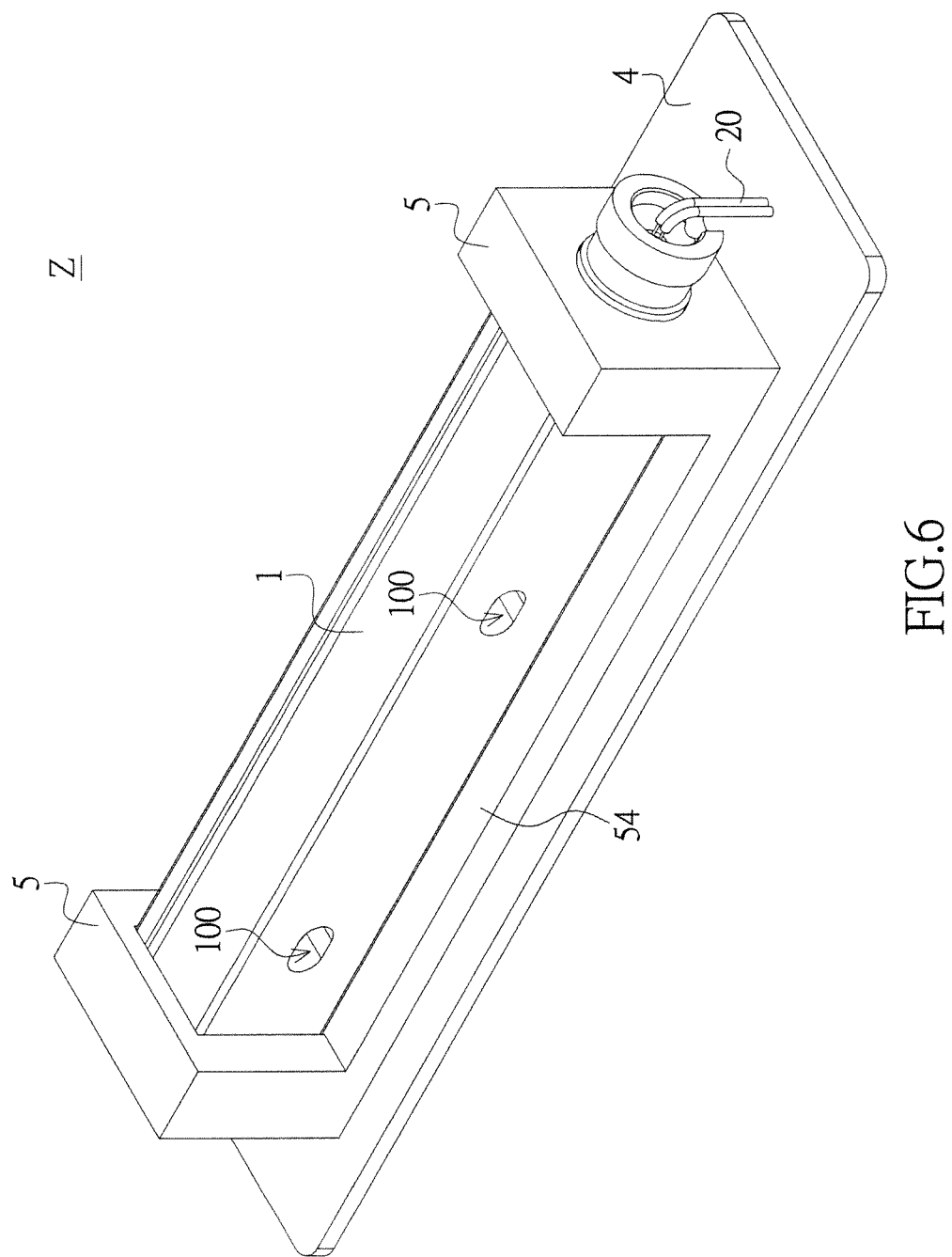
FIG. 6 is a perspective view of a gas sensor in accordance with a third embodiment of the instant disclosure.
Figure 7:
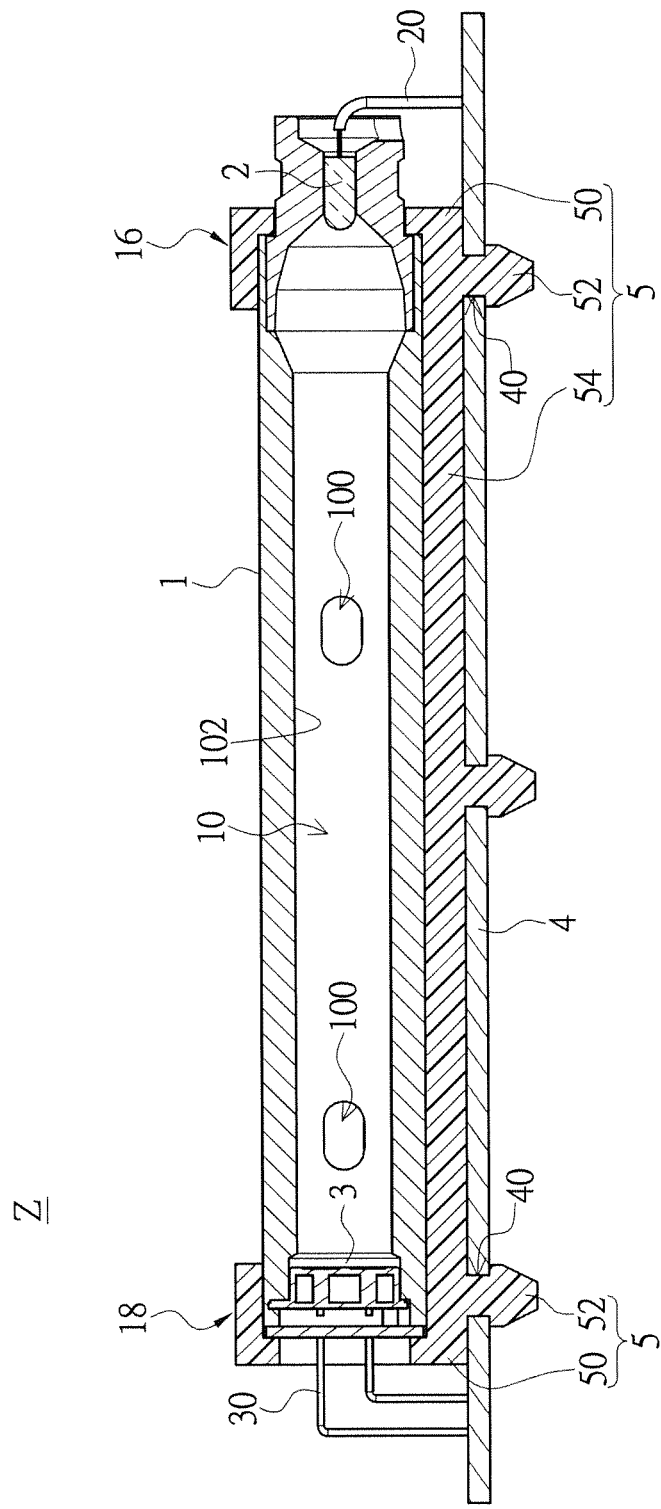
FIG. 7 is a cross-sectional view of a gas sensor in accordance with a third embodiment of the instant disclosure.

Please refer to FIGS. 6 to 7. FIG. 6 is a perspective view of the gas sensor Z. FIG. 7 is a cross-sectional view of the gas sensor Z. Comparing FIGS. 1 to 6 and 3 to 7, the gas sensor Z of the third embodiment includes a gas detector 1, an infrared source 2, an infrared detector 3, a circuit board 4, and at least one shockproof unit 5. The difference between the first and the third embodiment arises from a connection portion 54 between two shockproof units 5. The pair of shockproof unit 5 is further connected by the connection portion 54. The connection portion 54 is disposed between the chamber 10 and the circuit board 4 and connected to the chamber 10 and the circuit board 4.

Furthermore, the pair of the shockproof units 5 and the connection portion 54 are integrally formed. The shockproof unit 5 can be made by injection molding and be contiguous with the gas detector 1. In this regard, the shockproof unit 5 provides more effective shock protection, and the gas detector 1 is more firmly secured to the circuit board 4.

Fourth Embodiment

Figure 8:
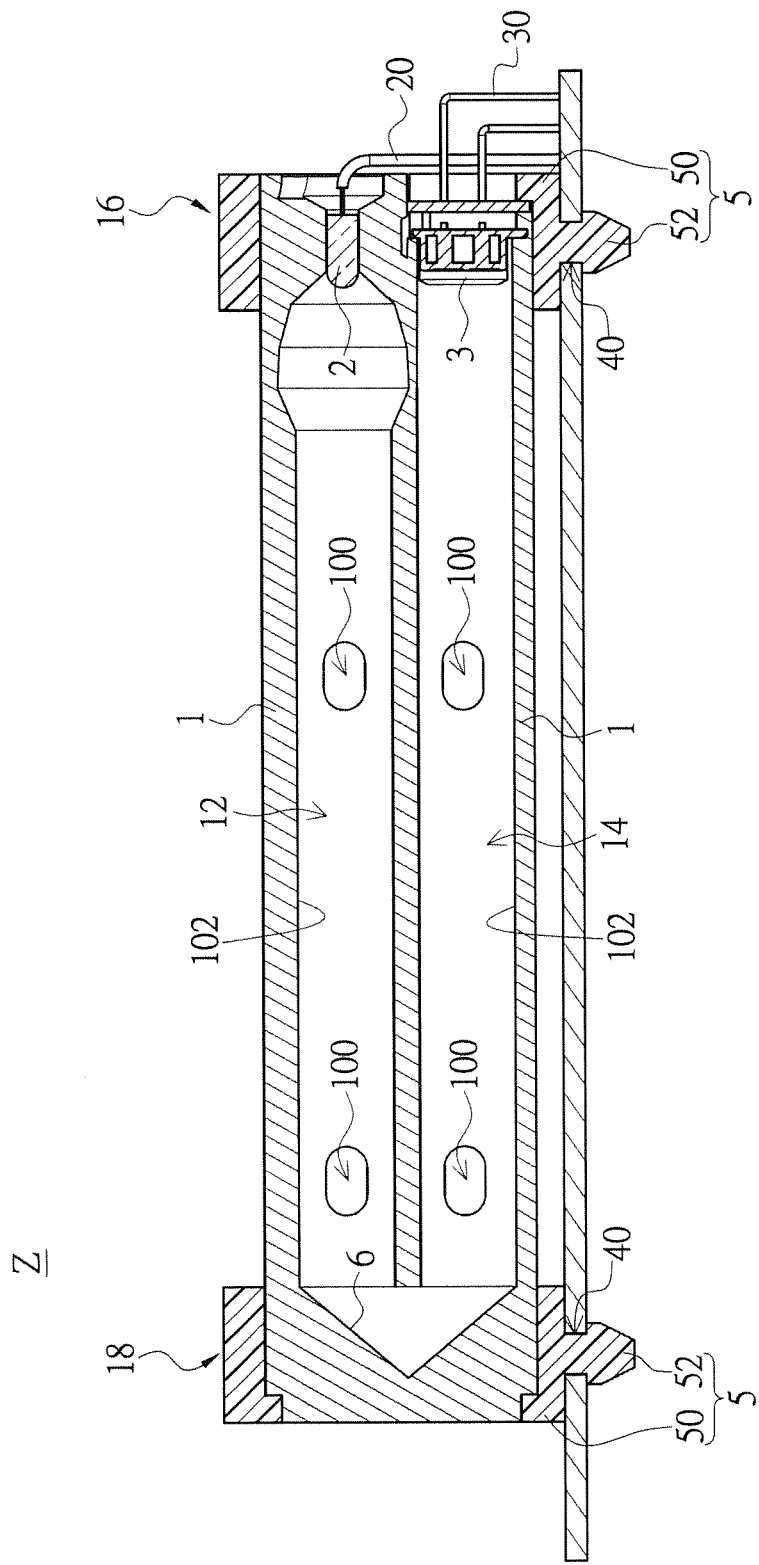
FIG. 8 is a cross-sectional view of a gas sensor in accordance with a fourth embodiment of the instant disclosure.

Please refer to FIG. 8. FIG. 8 is a cross-sectional view of the gas sensor Z. The gas sensor Z of the fourth embodiment includes a gas detector 1, an infrared source 2, an infrared detector 3, a circuit board 4, at least one shockproof unit 5 and a reflector 6. Comparing FIGS. 3 and 8, the difference between the first and the fourth embodiment is elaborated herein. In the fourth embodiment, the gas detector 1 defines an upper chamber 12 and a lower chamber 14 opposite the upper chamber 12. The gas detector 1 also has the first end portion 16 and a second end portion 18 opposite the first end portion 16. The infrared source 2 is disposed in the upper chamber 12 proximate to the first end portion 16. The infrared detector 3 is disposed in the lower chamber 14 proximate to the first end portion 16. The circuit board 4 is electrically and respectively connected to the infrared source 2 and infrared detector 3. The shockproof unit 5, the gas detector 1 and the circuit board 4 are connected to one another. The gas detector 1 is disposed on the circuit board 4 and connected thereto by the shockproof unit 5.

Specifically, the reflector 6 is coupled to the second end portion 18 of the gas detector 1. The upper and lower chambers 12, 14 are then in communication, forming a dual channel, because of the reflector 6. In the instant embodiment, two shockproof units 5 are coupled to the gas detector 1. One of the shockproof units 5 is coupled to the first end portion 16 of the upper and lower chambers 12, 14 from their outer face while the other shockproof unit 5 is coupled to the second end portion 18 thereof.

In addition, in another embodiment similar to the second embodiment, the gas detector 1 may include a plurality of shockproof units 5. Each shockproof unit 5 is spaced by a predetermined interval between the first and second end portions 16, 18. In still another embodiment similar to the third embodiment, the gas detector 1 includes two shockproof units 5 and the two shockproof units 5 have the connection portion 54 therebetween. The connection portion 54 connects the two shockproof units 5. The connection portion 54 is disposed between the lower chamber 14 and the circuit board 4 and connected to the lower chamber 14 and the circuit board 4. The configuration as shown in the fourth embodiment allows the dual-channel gas detector 1 to attach to the circuit board 4 by the shockproof unit 5 which absorbs shocks.

Fifth Embodiment

Figure 9:
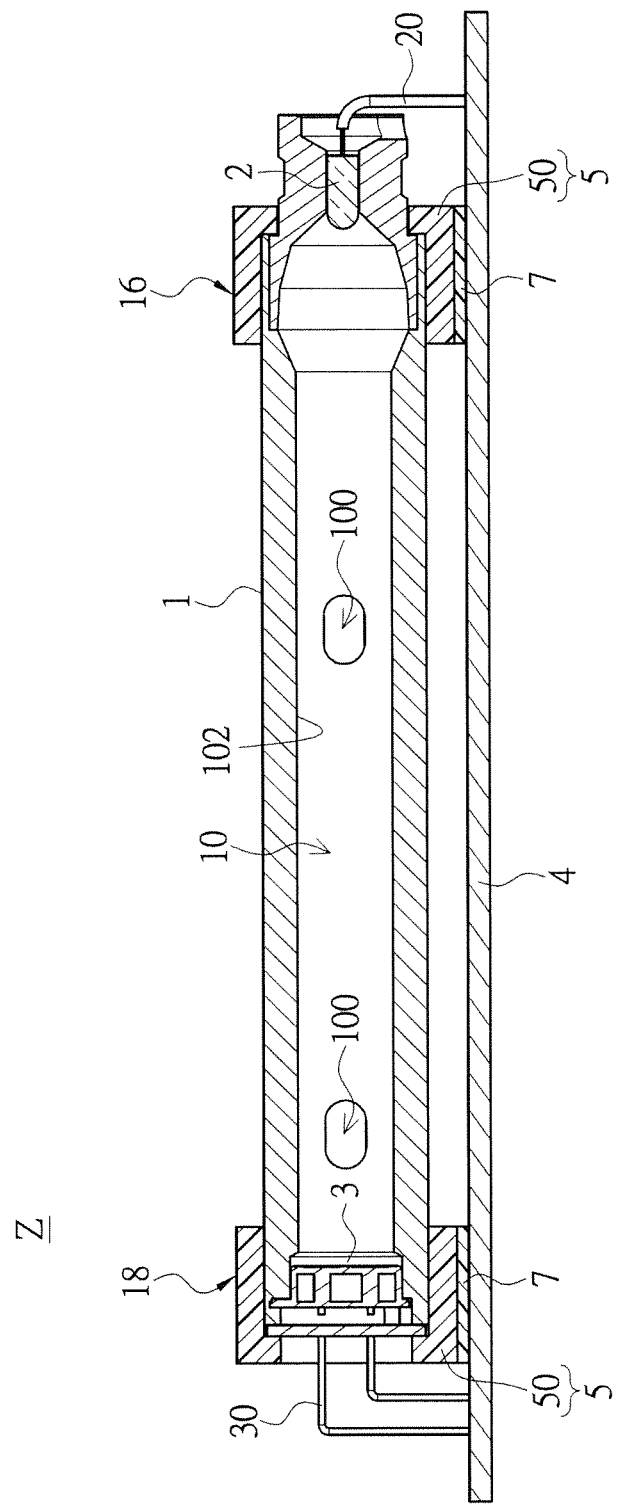
FIG. 9 is a cross-sectional view of a gas sensor in accordance with a fifth embodiment of the instant disclosure.

Please refer to FIG. 9. FIG. 9 is a cross-sectional view of the gas sensor Z. The gas sensor Z of the fifth embodiment includes a gas detector 1, an infrared source 2, an infrared detector 3, a circuit board 4, at least one shockproof unit 5 and an adhesive layer 7. Comparing FIG. 9 to FIGS. 3, 5, 7 and 8, the shockproof unit 5 sleeves the outer face of the chamber 10, acting as a buffer, and the shockproof unit 5 connects to the circuit board 4 through the adhesive layer 7, which provides firm attachment. Specifically, the adhesive layer 7 is formed by adhesive dripping, baking and curing.

In short, the shockproof gas sensor of the instant disclosure prevents the infrared detector from shifting or the infrared source from distortion upon shock or crash. The infrared distribution and the measurement precision are therefore maintained. This stability is supported by the shockproof unit connecting to the gas detector and the circuit board.

The descriptions illustrated supra set forth simply the preferred embodiments of the instant disclosure; however, the characteristics of the instant disclosure are by no means restricted thereto. All changes, alternations, or modifications conveniently considered by those skilled in the art are deemed to be encompassed within the scope of the instant disclosure delineated by the following claims.

What is claimed is:

1. A shockproof gas sensor comprising:
    a gas detector defining a chamber, a first end portion and a second end portion opposite the first end portion;
    an infrared source disposed in the chamber proximate to the first end portion;
    an infrared detector disposed in the chamber and proximate to the second end portion;
    a circuit board electrically connected respectively to the infrared source and the infrared detector; and
    at least one shockproof unit coupled to the gas detector and the circuit board, the gas detector being secured on the circuit board by the shockproof unit.

2. The shockproof gas sensor according to claim 1, wherein the shockproof unit includes a plurality of knobs and a buffer portion that sleeves the outer face of the chamber, and the circuit board is formed with a plurality of alignment holes for receiving the plurality of knobs in place.

3. The shockproof gas sensor according to claim 1, wherein the shockproof unit sleeves the outer face of the chamber and an adhesive layer is formed between the shockproof unit and the circuit board for tightly connecting the shockproof unit and the circuit board, and the adhesive layer is formed by adhesive dripping on the circuit board.

4. The shockproof gas sensor according to claim 1, wherein the quantity of the shockproof units is two, the two shockproof units sleeve the gas detector, and one of the shockproof units is coupled to the outer face of the chamber proximate to the first end portion while the other one of the shockproof units is coupled to the outer face of the chamber proximate to the second end portion.

5. The shockproof gas sensor according to claim 1, wherein a plurality of shockproof units sleeves the gas detector and each of the shockproof units is spaced by a predetermined distance between the first and second end portions.

6. The shockproof gas sensor according to claim 4, wherein the two shockproof units further have a connection portion connecting therebetween, the connection portion is disposed between the chamber and the circuit board and connected to the chamber and the circuit board.

7. A shockproof gas sensor comprising:
    a gas detector defining an upper chamber, a lower chamber opposite to the upper chamber, a first end portion and a second end portion opposite the first end portion;
    an infrared source disposed in the chamber proximate to the first end portion;
    an infrared detector disposed in the chamber proximate to the second end portion;
    a circuit board electrically connected respectively to the infrared source and the infrared detector;
    at least one shockproof unit coupled to the gas detector and the circuit board, the gas detector being secured on the circuit board by the shockproof unit; and
    a reflector coupled to the second end portion and connecting the upper and lower chambers.

8. The shockproof gas sensor according to claim 7, wherein two shockproof units sleeve the gas detector, and one of the shockproof units is coupled to the outer face of the upper and lower chambers proximate to the first end portion while the other one of the shockproof units is coupled to the outer face of the upper and lower chambers proximate to the second end portion.

9. The shockproof gas sensor according to claim 7, wherein a plurality of shockproof units sleeves the gas detector and each of the shockproof units is spaced by a predetermined distance between the first and second end portions.

10. The shockproof gas sensor according to claim 8, wherein the two shockproof units further have a connection portion connecting therebetween, the connection portion is disposed between the chamber and the circuit board and connected to the chamber and the circuit board.

\* \* \* \* \*